US00PP30547P2

(12) United States Plant Patent
Van Dijk

(10) Patent No.: US PP30,547 P2
(45) Date of Patent: May 28, 2019

(54) *ANTHURIUM* PLANT NAMED 'ANTHFABLO'

(50) Latin Name: ***Anthurium andraeanum* L.**
Varietal Denomination: ANTHFABLO

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,789

(22) Filed: Apr. 24, 2018

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./263.1, 365, 369
See application file for complete search history.

(56) References Cited

PUBLICATIONS

UPOV-PLUTO: Plant Variety Database, Jan. 8, 2019, citation for 'Anthfablo'. 1 page.*
EU Community Plant Variety Rights Application No. 2016/2940, Application n°A201603026, filed Nov. 25, 2016, 8 pages.
EU Community Plant Variety Office Official Gazette, I.2017, Feb. 15, 2017, cover page and pp. 30, 51.
Anthura *Anthurium* brochure, published Oct. 2017, 1 page.

* cited by examiner

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new *Anthurium* plant named 'ANTHFABLO' particularly distinguished by having shiny, orange, orbicular cordate and durable spathes that retain the original color for a very long period of time, dark green and ovate-cordate, durable leaves, white spadices with yellow tips, early and rich flowering continuously throughout the year, and a plant height of 35.0 cm to 40.0 cm is disclosed.

3 Drawing Sheets

Genus and species: *Anthurium andraeanum* L.
Variety denomination: 'ANTHFABLO'.

BACKGROUND OF THE NEW PLANT

The present invention comprises a new and distinct variety of *Anthurium*, botanically known as *Anthurium andraeanum* L., and hereinafter referred to by the variety name 'ANTHFABLO'. The new *Anthurium* plant is a product of a planned breeding program conducted by the inventor in Bleiswijk, the Netherlands. The objective of this breeding program was to create a new 35.0 cm to 40.0 cm height plant with shiny and blistered, orange, orbicular cordate and durable spathes.

The new variety originated from a cross-pollination made in December 2009 in Bleiswijk, The Netherlands. The female parent was an orange *Anthurium* pot plant designated '11548-02' (unpatented), and the male parent was an orange *Anthurium* pot plant designated '10867-04' (unpatented).

A single plant was selected from the progeny of the stated cross in January 2012 and has been asexually reproduced repeatedly by tissue culture in Bleiswijk, The Netherlands over a 4-year period. The present invention has been found to retain its distinctive characteristics through successive asexual propagations.

Plant Breeder's Rights for this variety have been applied for in the European Union on Nov. 25, 2016. 'ANTHFABLO' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Shiny and blistered, orange and orbicular cordate spathes;
2) White spadices with yellow tips;
3) Green, ovate-cordate leaves; and
4) Orange color of old flowers remains for a long period of time.

DESCRIPTION OF THE PHOTOGRAPHS

This new *Anthurium* plant is illustrated by the accompanying photographs which show the overall plant habit including blooms, bud and foliage of the plant; the colors shown are as true as can be reasonably obtained by conventional photographic procedures. The photographs are of a 44-week old plant grown in a greenhouse in Bleiswijk, The Netherlands in February 2018. Colors in the photographs may differ from the color values cited in the detailed botanical description, which accurately describe the actual colors of the new variety.

DESCRIPTION OF THE NEW VARIETY

Figure 1:
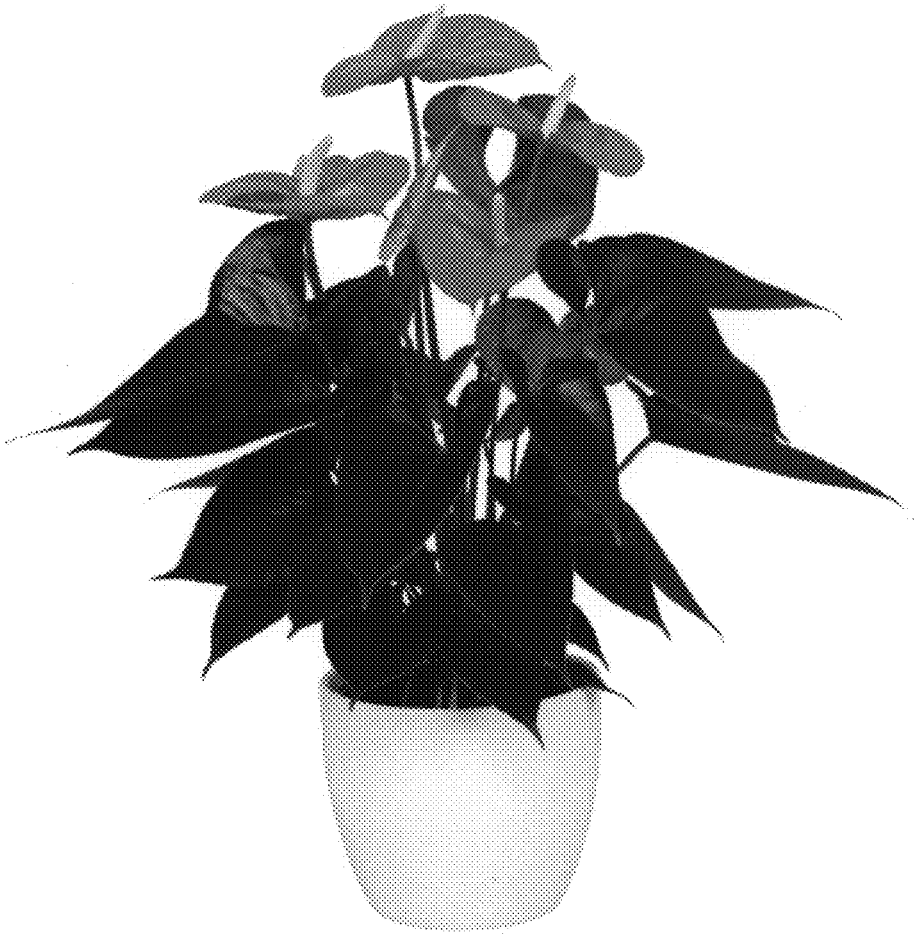
FIG. 1 shows the overall plant habit, including blooms, bud and foliage.
Figure 2:
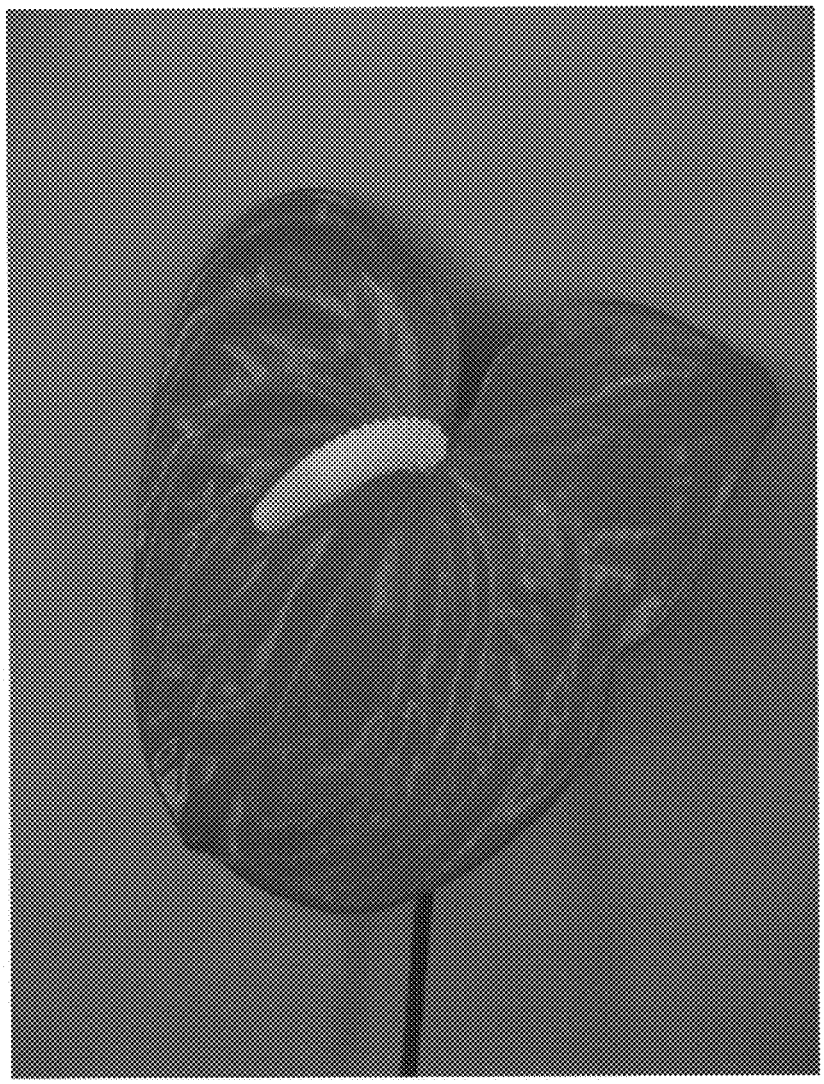
FIG. 2 shows a close-up of the mature spathe.
Figure 3:
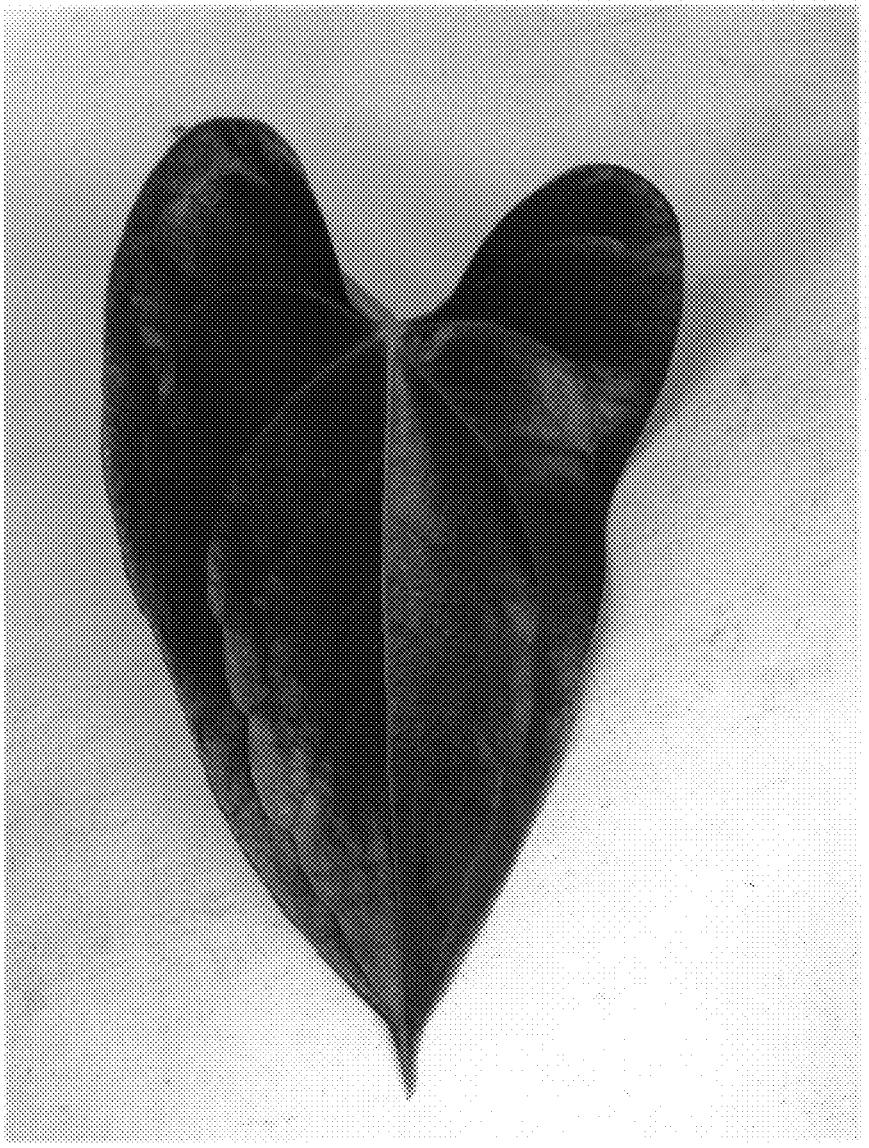
FIG. 3 shows a close-up of the upper leaf blade surface.

The following detailed description sets forth the distinctive characteristics of 'ANTHFABLO'. The data which define these characteristics were collected from asexual reproductions carried out in Bleiswijk, The Netherlands. The plant history was taken on 44-week old plants which were planted from tissue culture in 14 centimeter (diameter) pots and grown in a glass greenhouse between 19° C. and 24° C. Observations were made in February 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHFABLO'.

Parentage:

*Female parent*.—*Anthurium* plant '11548-02' (unpatented).

*Male parent*.—*Anthurium* plant '10867-04' (unpatented).

Plant:

*Propagation*.—Tissue culture.

*Root description*.—Fleshy light yellowish-pink colored roots with small hairy lateral roots having greenish-yellow colored root tips.

*Time to produce a finished flowering plant*.—42 to 46 weeks after planting in a 14 cm (diameter) pot.

*Growth habit*.—Upright.

*Height* (*measured from soil, including inflorescence*).—35.0 cm to 40.0 cm.

*Width* (*measured from leaf tips*).—39.0 cm to 44.0 cm.

Leaves:

*Immature leaves*.—Length: 10.0 cm to 12.0 cm. Width: 6.0 cm to 7.0 cm. Color: Upper surface: RHS 146A. Lower surface: RHS 146B with a touch of RHS 172B toward the tip. Texture (both upper and lower surfaces): Shiny.

*Mature leaves*.—Length (fully expanded): 17.0 cm to 19.0 cm. Width: 10.0 cm to 12.0 cm. Shape: Ovate-cordate. Apex: Acuminate. Base: Cordate. Leaf blade angle with the petiole: Between 110 degrees and 120 degrees. Leaf margin: Entire. Color: Upper surface: RHS 147A. Lower surface: RHS 146B. Texture (both upper and lower surfaces): Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144C.

*Lobes*.—Present. Arrangement: Leaf blade has two lobes extending past the petiole. The lobes are non-touching. Length of lobes of mature leaf blades: 2.0 cm to 3.0 cm. Width of lobes of mature leaf blades: 4.0 cm to 4.5 cm. Distance from petiole/leaf junction to highest point on lobes of mature leaf: 3.0 cm to 4.0 cm.

*Petiole*.—Cross-section: Round. Diameter: 0.3 cm to 0.4 cm. Length: 19.0 cm to 22.0 cm for a mature leaf size. Color: Mature leaf: RHS 144A. Immature leaf: RHS 144B. Cataphyll color surrounding the petiole: Outside: RHS 180A. Inside: RHS 180B/C.

*Geniculum*.—Length: 2.0 cm to 2.5 cm. Width: 0.3 cm to 0.4 cm. Color: RHS 144B.

Inflorescence:

*Arrangement*.—Single.

*Flowering habit* (*length of flowering season*).—Continuous.

*Number of inflorescences per plant*.—5 to 8.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters (approximately 1 to 3 extra centimeters).

*Arrangement*.—Spathe angle with the peduncle is between 70 degrees and 90 degrees; the spathe stands on a wiry peduncle about 5.0 cm to 10.0 cm above the foliage.

*Shape*.—Orbicular cordate.

*Apex*.—Mucronate.

*Base*.—Cordate.

*Texture*.—Shiny and blistered.

*Margin*.—Slightly undulated.

*Size*.—Length: 10.0 cm to 11.0 cm. Width: 10.0 cm to 11.0 cm.

*Lobes*.—Present.

*Arrangement*.—The spathe has two lobes extending past the peduncle. The lobes are non-touching. Length: 2.5 cm to 3.5 cm. Width: 4.5 cm to 5.5 cm.

*Color*.—Just fully open: Upper surface: RHS 44B. Lower surface: RHS 44C. This orange color remains for a very long period, at least more than 30 weeks after opening.

Peduncle:

*Shape*.—Erect.

*Cross-section*.—Round.

*Length*.—25.0 cm to 30.0 cm.

*Diameter*.—0.3 cm to 0.4 cm.

*Color*.—RHS 144B.

Flowering time:

*General*.—One small, rooted, untreated tissue culture plant of 8.0 cm tall will flower, depending on season, after 42 to 46 weeks and 5 to 6 blossoms appear. More blossoms appear after some additional weeks so that a full flowering and commercial plant will have 6 to 8 orange spathes. Smaller blossoms may occur on immature plants.

Spadix:

*Size*.—Length: 3.5 cm to 4.5 cm (depending on flower size). Width (at apex): 0.5 cm to 0.6 cm. Width (at base): 0.6 cm to 0.7 cm.

*Shape*.—Columnar.

*Angle from spadix tip to peduncle*.—130 degrees to 150 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 12B. Mature: RHS 155B. Ages to: RHS 151C.

Flowers:

*Quantity per spadix*.—130 to 180.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed to date.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

Disease and pest resistance: Under commercial conditions, no specific resistance to pathogens or pests common to *Anthurium* has been observed to date.

COMPARISON WITH PARENTAL AND COMMERCIAL VARIETIES

'ANTHFABLO' differs from the female parent plant '11548-02' (unpatented) in that 'ANTHFABLO' has red cataphyll and flat spathes, whereas '11548-02' has green cataphyll and wavy spathes. Additionally, 'ANTHFABLO' has a narrower angle of spadix tip with the peduncle than '11548-02'.

'ANTHFABLO' differs from the male parent plant '10867-04' (unpatented) in that 'ANTHFABLO' has red cataphyll and flat spathes, whereas '10867-04' has green cataphyll with red tips and cupped spathes. Additionally, 'ANTHFABLO' has a wider angle of spadix tip with the peduncle than '10867-04'.

'ANTHFABLO' differs from similar commercial variety 'ANTHZUPAP' (U.S. Plant Pat. No. 23,140) in that 'ANTHFABLO' has red cataphyll, blistered spathes and a narrow spadix angle to spathe, whereas 'ANTHZUPAP' has green cataphyll, unblistered spathes and a medium spadix angle to spathe. Additionally, 'ANTHFABLO' has larger spathes than 'ANTHZUPAP'.

'ANTHFABLO' differs from similar commercial variety 'ANTHECWIE' (unpatented) in that 'ANTHFABLO' has ovate-cordate leaves, blistered spathes and a narrow spadix angle to spathe, whereas 'ANTHECWIE' has elliptical cordate leaves, strongly blistered spathes and a wide spadix angle to spathe. Additionally, 'ANTHFABLO' has larger spathes than 'ANTHECWIE'.

I claim:

1. A new and distinct variety of *Anthurium* plant named 'ANTHFABLO', substantially as illustrated and described herein.

* * * * *